United States Patent
Dubey et al.

(10) Patent No.: US 8,337,911 B2
(45) Date of Patent: Dec. 25, 2012

(54) HERBAL FORMULATION FOR THE PREVENTION AND MANAGEMENT OF TYPE-2 DIABETES MELLITUS AND VASCULAR COMPLICATIONS ASSOCIATED WITH DIABETES

(75) Inventors: Govind Prasad Dubey, Varanasi (IN); Aruna Agrawal, Varanasi (IN); Nirupama Dubey, Kattankulathur (IN); Shipra Dubey, Kattankulathur (IN); Rajesh Dubey, Kattankulathur (IN); Samamtsan Mercy Deborah, Varanasi (IN)

(73) Assignee: SRM University, Kattankulathur (IN)

( * ) Notice: Subject to any disclaimer, the term of this patent is extended or adjusted under 35 U.S.C. 154(b) by 0 days.

(21) Appl. No.: 13/162,778

(22) Filed: Jun. 17, 2011

(65) Prior Publication Data
US 2012/0148692 A1    Jun. 14, 2012

(30) Foreign Application Priority Data

Jun. 18, 2010 (IN) .......................... 1708/CHE/2010

(51) Int. Cl.
*A01N 65/00* (2009.01)
(52) U.S. Cl. ....................................................... 424/725
(58) Field of Classification Search ........................ None
See application file for complete search history.

(56) References Cited

OTHER PUBLICATIONS

Salacia roxburghii, 1 page, 2012.*

* cited by examiner

*Primary Examiner* — Michael Meller
(74) *Attorney, Agent, or Firm* — Venable LLP; Keith G. Haddaway

(57) ABSTRACT

This invention relates to a novel herbal formulation for the prevention and management of type-2 diabetes mellitus and vascular complications associated with diabetes comprising, preparing of hydromethanolic extract of at least one plant selected form *Salacia roxburghii, Salacia oblonga, Garcinia Indica* and *Lagerstroemia parviflora* at 70°-80° C., maintaining ph of the solution between 7-10, separating the active compounds by using TLC, HPLC, HPTLC, subjecting the active compounds to the step of molecular characterization.

20 Claims, 2 Drawing Sheets

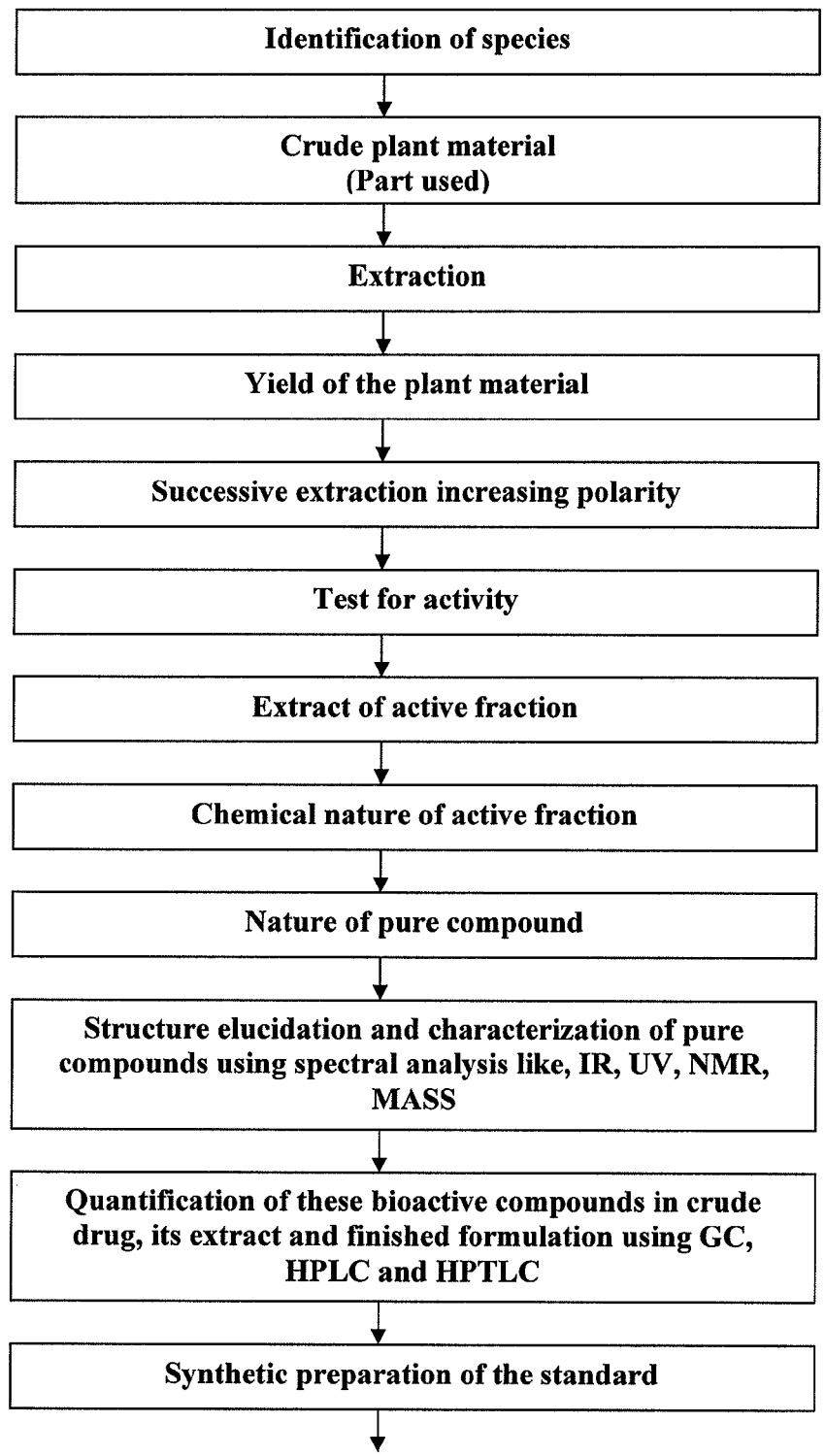

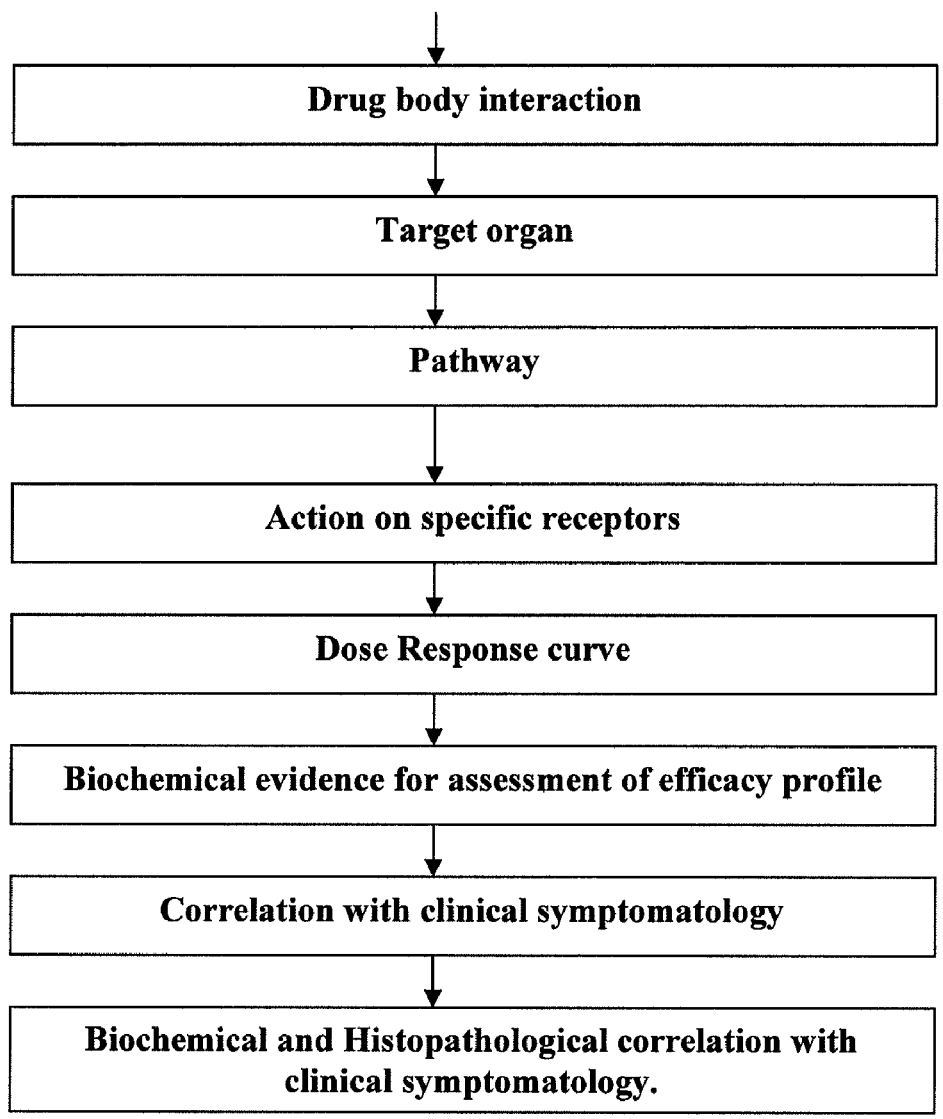

HERBAL FORMULATION FOR THE PREVENTION AND MANAGEMENT OF TYPE-2 DIABETES MELLITUS AND VASCULAR COMPLICATIONS ASSOCIATED WITH DIABETES

FIELD OF INVENTION

This invention relates to a novel herbal formulation for the prevention and management of type-2 diabetes mellitus and vascular complications associated with diabetes.

BACKGROUND OF INVENTION

Type-II diabetes mellitus (DM) is a metabolic disorder that is primarily characterized by insulin resistance, relative insulin deficiency and hyperglycemia. It is rapidly increasing in the developed countries and there is also evidence that this pattern will be followed in much of the rest of the parts of the world in coming years. About 90-95% of all North Americans are suffering from type-II diabetes and 20% of the population are over the age of 65 years. Diabetes affects over 150 million people worldwide and this number is expected to double by 2025. Now it has been proven that the Islet Amyloid Polypeptide genes are responsible for the early on set of type-II diabetes.

Type II diabetes is the predominant form of diabetes accounting for 90% of case globally. In type II diabetes, two impairments are found to increase blood glucose levels; impaired insulin action and impaired pancreatic insulin secretion. In addition, liver also plays key role in adjusting blood glucose levels via. gluconeogenesis in fasting and glucogenolysis in postprandial conditions. In type II diabetes glucogenolysis increases disproportionally which further contribute in elevated blood glucose level.

About 55% patients of type-II diabetes mellitus are obese, with the result obesity leads to increased insulin resistance that can develop into diabetes. Further, type-II diabetes mellitus often associated with obesity, hypertension and dyslipidemia. Additional factors founds to be associated with type-II diabetes include ageing, high fat diets and less active life style.

Diabetes is associated with factors which directly contribute to cardiovascular disorders including insulin resistance, dyslipidemia, atherosclerosis, hypertension, excessive oxidations, endothelial dysfunction, vascular inflammation and growth factors may affect platelet aggregation. Obesity is another risk factor in the development of diabetes and CHD.

Both diabetes and impaired glucose tolerance are associated with increased risk of reno-Cardio vascular diseases (CVD). Approximately 80% of death in diabetes patients are due to CVD which is significantly associated with dyslipidemia.

Inflammation plays a vital role in pathogenesis of CHD among diabetes patients. Interleukin-6 and C-reactive protein are scientific bio-markers associated with hyperglycemia, insulin resistance and type-2 diabetes mellitus. Both the factors are responsible for development of cardiovascular disorders. IL-6 has been shown to induce gluconeogenesis subsequently hyperglycemia and hyperinsulinemia. Levels of CRP are increased in type-2 diabetes and can cause CHD death independently. Hyperhomocysteinemia (Hyper Hcy) is also recognized as independent risk factor for CVD in type-2 diabetes. Hyper Hcy exerts toxic effects via elevated oxidative stress which induces endothelial dysfunction. In addition adipokine leptin has been found to be positively associated with insulin resistance, diabetes risk, triglyceride level, CRP, blood pressure, obesity etc. Adiponectin, a protein secreted by adipose cells regulates insulin sensitivity with energy metabolism. A decreased level of adiponectin concentration is recorded in above conditions. Recently peroxisome proliferator activator receptor (PPAR-α)-α and PPAR-γ are found to be associated with diabetes that regulated insulin responsive gene transcription involved in glucose production, transport and utilization.

The available oral anti-hyperglycemic drugs are in practice for the management of diabetes but application of these agents is limited because of adverse reaction of these synthetic chemicals.

Similarly treatment with statin for dyslipidemia causes risk of hepatic or muscle enzyme abnormalities.

Keeping the above facts in view it was thought to propose a plant based formulation showing beneficial role in the management of type-2 diabetes mellitus and associated disorder. In Ayurvedic system of medicine, several plants have been advocated for their hypoglycemic effects and are still in practice. Taking the lead from ancient literature four plants *Salacia roxburghii* (Saptarangi), *Salacia oblonga*, *Garcinia indica* (Kokum) and *Lagerstroemia parviflora* (Jarul) were selected out of various screened plants carried out for this purpose and the novel formulation was prepared following standard norms.

In experimental studies the safety and efficacy profile of single plant candidate and also combined formulation has been established. The test drug was found to have an agonist for PPAR activated receptor and regulates insulin responsive gene transcription involved in glucose production, transport and utilization and thus reduced blood glucose and reduces hyper-insulinemia. Our claims are established on the basis of experimental and clinical trials.

OBJECTS OF INVENTION

The main object of this invention is to propose plant based herbal formulation in the prevention and management of type-2 diabetes mellitus and associated vascular complications with the purpose of preventing CHD death among diabetic patients.

Another object of present invention is to propose a plant based Ayurvedic formulation showing role as an agonist for PPAR activated receptor and can regulate insulin responsive gene transcription.

Still, another object of present invention is to propose an Ayurvedic formulation showing beneficial role on abnormal lipid metabolism (dyslipidemia) particularly oxidized LDL and triglycerides among type-2 diabetes cases.

Yet another object of present invention is to propose a novel formulation which can retard the pro-inflammatory markers TNF-α, IL-6 and also CRP in type-2 diabetes cases.

Another object of present invention is to propose a plant based formulation showing beneficial role in increasing adiponectin among type-2 diabetes cases to prove the anti-obesity and anti-atherosclerotic property of present novel formulation.

Further, object is to propose a plant based formulation effective in the prevention and management of hyperglycemia, ultimately that can prevent major organ system i.e. brain, heart, kidney in diabetic patients.

STATEMENT OF INVENTION

According to this invention there is provided a novel herbal formulation for the prevention and management of type-2 diabetes mellitus and vascular complications associated with diabetes comprising hydromethanolic extract of at least one plant out of four plants i.e *Salacia roxburghii, Salacia oblonga, Garcinia indica* and *Lagerstroemia parviflora* in effective doses and a process for the preparation of thereof comprising; preparation of hydro-methanolic extract of *Salacia roxburghii* and *Lagerstroemia parviflora* by mixing aqueous and methanol in 30:70 ratio at 70-80° C., maintaining pH of the solution between 7-10, separating chromatographically active compounds/molecules by using TLC, HPLC, HPTLC, molecular characterization by using IR and NMR separating the active chemical constituents present in plants.

BRIEF DESCRIPTION OF THE FIGURES

FIG. 1 is a flow diagram of the process.

DETAILED DESCRIPTION OF INVENTION

The present invention relates to the novel Ayurvedic formulation and to the process thereof for the prevention and management of dyslipidemia, atherosclerosis, obesity, and endothelial dysfunction in type-2 diabetes mellitus cases. The preparation of present invention is advantageous if used for the prevention and management of hyperglycemia, abnormal lipids, altered adipokines, elevated inflammatory cytokines, obesity, hyperhomocystinemia, hypertension and atherosclerosis involved with diabetic patients. The beneficial role of novel Ayurvedic formulation can be assessed on blood glucose level, as an agonist PPAR-α activated receptor activity, inflammatory pro-cytokines including CRP, adipokine, adiponectin, homocysteine, oxidized LDL-c, triglycerides and endotheline level.

The hydro-methanolic extract of four Ayurvedic plants *Salacia roxburghii, Salacia oblonga, Garcinia indica* and *Lagerstroemia parviflora* by using 30:70 ratio of water and methanol respectively is used for the experimental and clinical studies. The water utilized for extraction was decontaminated for any type of bacterial or abnormal growth by using reverse osmosis plant. After extraction the active molecules was identified and separated by HPLC, HPTLC and NMR procedures.

The biological activity was studied on the basis of mode of action of the test drug and effect of the drug on various parameters undertaken for this clinical condition. The molecular characterization was done by using. NMR and bio-molecular reaction following the interaction between the chemical and biological markers like insulin resistance (blood glucose levels), inflammatory cytokines, adipokines, various fractions of lipids including triglycerides, the PPAR-α and PPAR-γ.

The pre-clinical toxicological studies were carried out to determine the safety profile of individual plant candidate as well as all four plant candidates combined to prepare novel formulation before using the drug for human beings. The mode of action of single plant and combined formulation was carried out in animal models.

The beneficial role of test formulation on fasting and post-prandial blood glucose level, PPAR-α agonist activity, insulin resistance, abnormal lipids, atherosclerosis, altered adipokines and inflammatory cytokines etc. were established in animal models before using the drug for human consumption.

Mechanism of Action of Present Formulation:

The present formulation containing the hydro-methanolic extract of *Salacia roxburghii, Salacia oblonga, Garcinia indica* and *Lagerstroemia parviflora* has shown anti-diabetic property in various experimental and clinical trials. The present formulation contains phyto-molecules that target various receptors responsible for diabetes. It is agonist for the PPAR-α & γ, with the result circulating level of triglycerides, LDL-c and total cholesterol decreases. It has been observed that extract of *Salacia roxburghii* enhances the level of PPAR-α mediated lipogenic gene expression resulting in the decreased level of triglycerides, oxidized LDL and total cholesterol.

The mode of action of present formulation is similar to the action of statin. The test formulation significantly influences the starch metabolizing enzyme as it reduces the hexokinase and lactate dehydrogenase. These liver enzymes play a major role in the metabolism of glucose.

Mangiferine and corosolic acid both have shown significant effect in reducing glycemic index both in animals and human subjects. Salcinol an important phyto-constituents found in *Salacia roxburghii* and *Salacia oblonga* have shown inhibition of cardiac angiotensin-II type-I receptor preventing the atherosclerosis and endothelial dysfunction thus prevents vascular changes in diabetes patients.

Extraction Procedure:

The shed dried root and fruits of *Salacia roxburghii, Salacia oblonga*, fruits and seeds of *Garcinia indica* and bark of *Lagerstroemia parviflora* were utilized for obtaining extracted material of the plants. The water and methanol extract (30:70 ratio) were utilized for the extraction of active compound found in the plants. After extraction the extracted materials were taken for chromatographic separation by using TLC, HPLC, and HPTCL. After identification and separation of the active compound the molecular characterization was carried out by using IR and NMR.

The extraction was done at the temperature of 70-80° c. The pH of the solution was maintained between 7-10. The following steps were followed and carried out to isolate the active compound, preparation of test drug as well as to develop a new drug entity. FIG. 1 is a flow diagram showing the steps involved in the extraction.

According to this invention there is provided an Ayurvedic formulation for the prevention and management of type-2 diabetes mellitus and associated vascular complications with the object to prevent the diabetic patients from CHD death and also from various type of morbidity caused due to hyperglycemia. The present test formulation comprising of the following four ingredients—

|   | Name of the plants | Part used |
|---|---|---|
| 1. | *Salacia roxburghii* (Saptarangi) | Root and fruits |
| 2. | *Salacia oblonga* (Saptachakra) | Root |
| 3. | *Garcini indica* (Kokum) | Fruits & Seeds |
| 4. | *Lagerstroemia parviflora* (Jarul) | Leaves |

Preferably the aforesaid plants are present in the test drug in following doses—

|   | Name of the plants | Dose |
|---|---|---|
| 1. | *Salacia roxburghii* | 225-400 mg/day |
| 2. | *Salacia oblonga* | 200-425 mg/day |
| 3. | *Garcinia indica* | 175-300 mg/day |
| 4. | *Lagerstroemia parviflora* | 175-325 mg/day |

The formulation may also comprise known additives such as minerals, vitamins, salts, filler (for capsulation or to prepare syrup) and binders, if required to present in trace amount.

Thus any known additive or supplement is added to prepare the final formulation as required and present in trace amount. Reference is made here in capsule form. However, it would be apparent that the preparation may also be in the form of syrup/tablet.

Preferably but without implying any limitation the preparation comprises—

|   | Name of the plants | Dose |
|---|---|---|
| 1. | Salacia roxburghii | 275 mg/day |
| 2. | Salacia oblonga | 325 mg/day |
| 3. | Garcinia indica | 225 mg/day |
| 4. | Lagerstroemia parviflora | 225 mg/day |

Hypothesis:

The present Ayurvedic formulation is based on the combined effect of four plant extract namely *Salacia roxburghii, Salacia oblonga, Garcinia indica* and *Lagerstroemia parviflora*. This novel formulation is an agonist for PPAR receptor, modified abnormal lipids including triglyceride, reduced inflammatory cytokines, regulates adipokines, and improves renal cardiac functions. Those effect are mediated through PPAR-α & γ against activity that results in insulin responsive gene transcription involved in glucose production, transport and utilization ultimately reduces blood glucose level, reduces inflammatory process by reducing CRP, IL-6, TNF-α, it regulates abnormal lipids including triglycerides concentration, enhances adiponectin and also reduces homocysteine. All these beneficial effects ultimately slowed down/improved atherosclerotic process among diabetes patients and has potential role in prevention of adverse cardiac event.

As documented diabetes increases the risk of myocardial infarction and risk of stroke, it is hypothesized that present test formulation improves the glycemic load by improving insulin sensitivity, as an agonist for PPAR-α activated receptors, stimulates beta-cells, increases glucose uptake in tissues, may have activity on cathepsin-b and increases cyclic AMP count on islets. As synergism test drug has anti-oxidant effects.

Atherosclerosis occurs due to a number of factors in diabetic individuals. Both insulin resistance and elevated lipid levels are the triggering factors for athrogenic injury, endothelial dysfunction in diabetics otherwise is more prone to atherogenic injury due to decreased production of endothelial nitric oxide and increased production of plasminogen activator inhibitor. Lipid disorders like elevated total cholesterol, low HDL-c and high triglyceride level is the major risk factor for CHD. Therefore, the prevention and management of vascular complications is the basic and essential principle among diabetes patients to prevent them from CHD death.

As the present test formulation contains of extracts of four plants *Salacia roxburghii, Salacia oblonga, Garcinia indica* and *Lagerstroemia parviflora* therefore, to describe the action of individual plant is helpful in understanding the specific action on specific target involved in diabetes. Garcinia indica extract contained 0.67 percent of garcinol and 0.17 percent of hydroxycitric acid. ((−)-Hydroxycitric acid (−)-HCA) has a potential effect in stimulating beta cells of islet langerhans. Similarly gracinol have shown potential effect in reducing pro-inflammatory cytokines mainly responsible for endothelial dysfunction among diabetic patients. The corosilic acid present in extract of *Lagerstroemia parviflora* in the dose of 1.02 percent showed potential effect in minimizing the inflammatory markers in type-2 diabetes mellitus cases. The proportion of mangiferin and salacinol varies in *Salacia roxburghii* and *Salacia oblonga*. The *Salacia roxburghii* exerted more potential effect in the prevention and management of diabetic complications particularly the vascular complications. The Salacia oblonga has specific action in regulation of postprandial glycemic index, PPAR-α & γ as well as it prevents the cardiac hypertrophy by regulating angiotensin-II receptors. Mangiferin modulates the liver enzyme like hexokinase, lactate dehydroxygenase, pyruvate kinase and also the metabolizing enzyme glucose-6-phosphatase, fructose-6bisphosphatase, glucose-6phosphatase dehydrogenase. Therefore, it is proven that combined formulation acted on different targets involved in type-2 diabetes mellitus.

C-peptide has no relation with blood glucose level but it has strong relationship with status of glomerular damage in diabetes. It has been demonstrated that C-peptide infusion increases the utilization of glucose among the diabetic patients. In healthy individuals C-peptide level indicates the better renal function suggesting measurement of C-peptide level might be helpful in the prevention of renal complications among diabetes.

The present novel Ayurvedic formulation has been developed on the basis of hypothesis that certain plants having bio-molecules responsible for enhancing the general body resistance by arresting the process of inflammation, catabolism and preventing oxidative damage due to reactive oxygen species. It is postulated that some of the plant based products have potentiality to prevent the comments complications like neuropathy, retinopathy and nephropathy associated with diabetes. It has been observed that adiponectin induces TNF-α, IL-6 and promotes tolerance to itself and other pro-inflammatory stimuli. It has been considered as an important biomarker for insulin resistance, obesity and generalized atherosclerotic changes in body. Therefore our main target is to find out the specific target which can arrest inflammation and prevents various complications associated with type-2 diabetes mellitus.

The investigators have established that combined formulation of above mentioned plants in specific dose not only enhances the level of adiponectin but also reduces the glycemic index and prevents from damage of vital organs by reducing inflammatory cytokines responsible for the endothelial dysfunction in type-2 diabetes mellitus. Adiponectin the important biomarker has potentiality to regulate multiple targets involved in type-2 diabetes mellitus.

About the Plants:

1. *Salacia roxburghii*: Mainly found in Eastern part of India. *Salacia* species belongs to family Hippocrastaceae. Fruits and root are used for medicinal purpose. Salaretin is the main active compound isolated from this plant is responsible for breakdown of starch in diet. Mangiferin is also an important component of *Salacia roxburghii*. This drug has shown anti-diabetic, anti-inflammatory, anti-oxidant, anti-obesity and homocysteine lowering activity in diabetes patients. Further, the drug enhanced PPAR-α—mediated lipogenic gene expression. Mangiferin lowers blood lipids in diabetes.

2. *Salacia oblonga*: Mainly found in Eastern part of India & Sri Lanka. *Salacia* species belongs to family Hippocrastaceae. The roots and stems of Salacia oblonga have been used extensively in Ayurveda and traditional Indian medicine for the treatment of Diabetes. Historically, *Salacia oblonga* is in use from the centuries by traditional practitioners. Recently, *Salacia oblonga* is being used to treat diabetes as it seems to lower blood sugar and insulin levels in a manner similar to prescription drugs. After recent pharmacological investigations it has been proved that *Salacia* roots modulate multiple targets mainly; peroxisome proliferator-activated receptoralpha-mediated lipogenic gene transcription, angiotensin II/angiotensin II type 1 receptor, alpha-glucosidase, aldose reductase and pancreatic lipase. The multi-targeted actions of *Salacia* root ultimately induced the improvements in type 2 diabetes mellitus and obesity-associated hyperglycemia, dyslipidemia and other related cardiovascular complications.

3. *Garcinia indica* (Kokum):

Belongs to the family Clusiaceae. Seeds and fruits of *Garcinia indica* is used for medicines and cosmetics. Hydroxycitric acid (HCA) is extracted from the rind of the fruit which is used as hypocholesterolaemic agent. It is also a potential anti-obesity agent. The anti-oxidant property of aqueous extract of the plant is observed. *Garcinia indica* extract is having anti-allergic effects. It contains oxalicacid, malic acid, polyphenols, carbohydrates, anthocyanin and ascorbic acid. Anti-oxidant property is due to Garcinol. Isogarcinol also shows anti-inflammatory, lipase inhibitor, anti-obesity and neuroprotective effect.

4. *Lagerstroemia parviflora* is commonly known as Jarul belongs to family Lytheraceae. It is very common tree found in the moist and dry forest mainly of Andhra Pradesh. The active compounds found in *Lagerstroemia parviflora* are—Flosin-B, Stachyurin, Casuarinin, casuarin, epipunicacortein-A, ellargic acid, corosolic acid, tannin etc. Leaves possess anti-diabetic, antibacterial, anti-obesity, anti-oxidant effects. It maintains the normal weight, promotes healthy insulin level. According to recent studies it increases glucose uptake and has positive role in glycemic control. The chemical constituents mainly ellagic acid has shown an inhibitory effect on glucose transport assay. The other active compounds corosolic acid has exhibited potent anti-diabetic activity as it reduced both fasting and postprandial blood glucose level.

EXAMPLE-I

In non-clinical efficacy profile evaluation when the hydro-methanolic extract of *Salacia roxburghii* in the dose of 50 mg/kg and *Lagerstroemia parviflora* 50 mg/kg and *Garcinia indica* 40 mg/kg was given to streptozotocin induced diabetic rats, the drug exerted as an agonist for PPAR activated receptors resulting in insulin regulated gene transcription.

EXAMPLE-II

When the hydro-methanolic extract of *Salacia roxburghii* 50 mg/kg and *Salacia oblonga* 50 mg/kg was given to Sprague Dawley rats, 63 percent α-glucosidase inhibitory activity was recorded. Further, amylase and lipid lipase lowering effects were also noticed.

EXAMPLE-III

When the hydro-methanolic extract of *Salacia roxburghii* 60 mg/kg and Garcinia indica 60 mg/kg was given to streptozotocin induced diabetic rats a significant reduction in blood glucose level was measured indicating anti-diabetic role of the drug.

EXAMPLE-IV

In clinical study when the hydro-methanolic extract of *Salacia roxburghii* in the dose of 525 mg/day and *Lagerstroemia parviflora* 350 mg/day combined and given in two divided doses to diagnosed cases of type-2 diabetes a significant decrease in postprandial blood glucose level was noticed. An average 40 percent depletion of blood glucose level indicated the anti-diabetic activity of test drug.

EXAMPLE-V

When the hydro-methanolic extract of *Salacia oblonga* (475 mg/day) and *Lagerstroemia parviflora* (450 mg/day) was mixed and given to type-2 diabetes patients a marked decrease in triglycerides content was estimated along with glycemic control property of the test formulation as glycosylated hemoglobin improved following treatment in diabetes patients.

EXAMPLE-VI

When the hydro-methanolic extract of *Garcinia indica* 250 mg/day, *Lagerstroemia parviflora* (325 mg/day) and *Salacia oblonga* (325 mg/day) mixed and administered to type-2 diabetes patients a significant decrease in Apolipo-B and moderate increase in HDL-c level was noticed.

EXAMPLE-VII

When the hydro-methanolic extract of *Garcinia indica* 250 mg/day, *Lagerstroemia parviflora* (350 mg/day) and *Salacia roxburghii* (350 mg/day) mixed and given to diagnosed cases of type-2 diabetes patients the oxidized LDL-c level decreased indicating improvement in atherosclerotic process among type-2 diabetes patients.

EXAMPLE-VIII

When the hydro-methanolic extract of *Salacia roxburghii* (325 mg/day) and *Lagerstroemia parviflora* (275 mg/day) and *Salacia oblonga* (350 mg/day) was mixed and given to diabetes patients decrease in pro-inflammatory markers like IL-6, TNF-α including hs. CRP was estimated indicating improvement in vascular inflammation in diabetes cases. It also reduces inflammatory marker resistin in diabetic patients.

EXAMPLE-IX

When the hydro-methanolic extract of *Salacia oblonga* (450 mg/day) and *Lagerstroemia parviflora* (450 mg/day) was mixed and administered to selected diabetes patients increase in adiponectin level indicated the anti-atherosclerotic and anti-obesity role of test formulation.

EXAMPLE-X

When the hydro-methanolic extract of *Salacia roxburghii* (275 mg/day), *Lagerstroemia parviflora* (225 mg/day), *Salacia oblonga* (325 mg/day) and *Garcinia indica* (225 mg/day) mixed and orally administered to selected type-2 diabetes patients a better effect of test formulation was recorded as the blood glucose level decreased, abnormal lipids modified including apolipo-B, the inflammatory cytokines IL-6 and TNF-α decreased, CRP and leptin also reduced, where as adiponectin level increased. On the whole this novel combined formulation has shown potential role in the prevention and management of type-2 diabetes mellitus and associated vascular complications through regulation of PPAR-α and PPAR-γ resulting in glycemic control and enhancing insulin sensitivity. Thus it is proposed as a better safer remedial measure for the prevention and management of type-2 diabetes mellitus and associated vascular complications in diabetes patients thus CHD death can be prevented among diabetes patients.

Alpha-glucosidase inhibitory activity of single as well as combined formulation

| Concentration (µg/ml) | Percent inhibition | | | | |
|---|---|---|---|---|---|
| | *Salacia roxburghii* | *Lagerstroemia parviflora* | *Salacia oblonga* | *Garcinia indica* | Combined formulation |
| 50 mg/kg | 23.79 | 28.72 | 28.40 | 25.03 | 31.61 |
| 100 mg/kg | 37.82 | 43.09 | 39.61 | 23.75 | 61.80 |
| 150 mg/kg | 41.6 | 48.22 | 46.22 | 25.85 | 72.32 |

Experimental Study-I

TABLE 1

Reduction in blood glucose level following test drug treatment in Streptozotocin (STZ) treated diabetic rats

| Treated group | Blood glucose level (mg/dl) | | |
|---|---|---|---|
| | $7^{th}$ Days | $14^{th}$ Days | $30^{th}$ Days |
| Normal control (N = 6) * | 63.91 ± 8.73 | 61.94 ± 10.11 | 64.82 ± 12.04 |
| Td. With STZ (65 mg/kg) N = 6 ** | 334.74 ± 28.99 | 293.71 ± 31.22 | 268.45 ± 37.02 |
| Td. With STZ + Test drug (N = 6)*** | 258.97 ± 22.84 | 209.85 ± 26.90 | 172.75 ± 21.65 |
| Td. With STZ + Acarbose **** | 237.90 ± 21.64 | 194.93 ± 16.87 | 164.35 ± 12.86 |
| Comp. | | | |
| * vs ** | $P < 0.001$ | $P < 0.001$ | $P < 0.001$ |
| ** vs*** | $P < 0.001$ | $P < 0.001$ | $P < 0.001$ |
| ***vs **** | $P > 0.05$ | $P < 0.05$ | $P < 0.05$ |

TABLE 2

Reduction in hs C-reactive protein following test drug treatment in STZ treated diabetic rats

| Treated group | hs CRP (mg/L) | | |
|---|---|---|---|
| | $7^{th}$ Days | $14^{th}$ Days | $30^{th}$ Days |
| Normal control (N = 6) * | 1.51 ± 0.24 | 1.43 ± 0.30 | 1.38 ± 0.45 |
| Td. With STZ (65 mg/kg) N = 6 ** | 9.11 ± 2.04 | 8.83 ± 2.12 | 6.89 ± 1.72 |
| Td. With STZ + Test drug (N = 6)*** | 7.34 ± 1.54 | 5.73 ± 0.84 | 4.08 ± 0.74 |
| Td. With STZ + Acarbose **** | 7.58 ± 1.61 | 5.85 ± 0.68 | 5.11 ± 0.93 |
| Comp. | | | |
| * vs ** | $P < 0.001$ | $P < 0.001$ | $P < 0.001$ |
| ** vs*** | $P < 0.001$ | $P < 0.001$ | $P < 0.001$ |
| ***vs **** | $P > 0.05$ | $P > 0.05$ | $P > 0.05$ |

TABLE 3

Reduction in Interleukin-6 following test drug treatment in STZ treated diabetic rats

| Treated group | IL-6 (pg/ml) | | |
|---|---|---|---|
| | $7^{th}$ Days | $14^{th}$ Days | $30^{th}$ Days |
| Normal control (N = 6) * | 0.83 ± 0.11 | 0.91 ± 0.13 | 0.87 ± 0.20 |
| Td. With STZ (65 mg/kg) N = 6 ** | 4.13 ± 1.02 | 3.94 ± 0.92 | 3.54 ± 0.88 |
| Td. With STZ + Test drug (N = 6)*** | 2.65 ± 0.24 | 2.16 ± 0.31 | 1.73 ± 0.27 |
| Td. With STZ + Acarbose **** | 2.94 ± 0.26 | 2.58 ± 0.30 | 2.21 ± 0.29 |
| Comp. | | | |
| * vs ** | $P < 0.001$ | $P < 0.001$ | $P < 0.001$ |
| ** vs*** | $P < 0.001$ | $P < 0.01$ | $P < 0.001$ |
| ***vs **** | $P > 0.05$ | $P > 0.05$ | $P > 0.05$ |

TABLE 4

Effect of test formulation on adiponectin level in STZ treated diabetic rats

| Treated group | Adiponectin (µg/ml) | | |
|---|---|---|---|
| | $7^{th}$ Days | $14^{th}$ Days | $30^{th}$ Days |
| Normal control (N = 6)* | 13.45 ± 1.87 | 14.13 ± 2.06 | 14.42 ± 2.11 |
| Td. With STZ (65 mg/kg) N = 6 ** | 6.86 ± 1.13 | 5.83 ± 0.97 | 5.09 ± 0.86 |
| Td. With STZ + Test drug (N = 6)*** | 9.11 ± 2.04 | 10.12 ± 1.75 | 12.93 ± 2.14 |
| Td. With STZ + Acarbose **** | 8.83 ± 2.02 | 9.82 ± 1.65 | 10.66 ± 2.01 |
| Comp. | | | |
| *vs ** | $P < 0.001$ | $P < 0.001$ | $P < 0.001$ |
| ** vs*** | $P < 0.05$ | $P < 0.001$ | $P < 0.001$ |
| ***vs **** | $P > 0.05$ | $P > 0.05$ | $P > 0.05$ |

Experimental Study-II

TABLE 1

Effect of Test formulation on body weight following cafeteria diet in experimental rats

| Treated group | Body Weight (grams) | | | Comp. Initial vs After 30 days |
|---|---|---|---|---|
| | Initial | After 15 Days | After 30 Days | |
| Normal control (N = 6) | 104.93 ± 3.88 | 110.82 ± 6.03 | 117.36 ± 4.91 | $P < 0.001$ |
| Cafeteria diet only (N = 6) | 99.22 ± 4.37 | 128.92 ± 6.11 | 158.90 ± 12.13 | $P < 0.001$ |
| Cafeteria diet + test formulation (N = 6) | 114.97 ± 9.82 | 119.93 ± 8.41 | 128.72 ± 7.04 | $P < 0.001$ |

TABLE 2

Effect of Test formulation on total cholesterol and triglycerides following cafeteria dies in experimental animals

| Treated group | TC (mg/dl) Initial | After 30 Days | Comp. Initial vs After 30 days | TG (mg/dl) Initial | After 30 Days | Comp. Initial vs After 30 days |
|---|---|---|---|---|---|---|
| Normal control (N = 6) | 84.78 ± 4.69 | 88.36 ± 5.11 | P > 0.05 | 81.89 ± 8.63 | 83.01 ± 9.34 | P > 0.05 |
| Cafeteria diet only (N = 6) | 87.11 ± 6.94 | 91.35 ± 9.12 | P < 0.05 | 79.74 ± 5.80 | 98.34 ± 4.93 | P < 0.05 |
| Cafeteria diet + test formulation (N = 6) | 86.90 ± 8.30 | 81.45 ± 6.03 | P < 0.05 | 83.22 ± 8.91 | 74.90 ± 7.85 | P < 0.05 |

TABLE 3

Effect of Test formulation on body weight following cafeteria dies in experimental rats

| Treated group | Blood glucose level (mg/dl) Initial | After 30 Days | Comp. Initial vs After 30 days | Adiponectin (µg/ml) Initial | After 30 Days | Comp. Initial vs After 30 days |
|---|---|---|---|---|---|---|
| Normal control (N = 6) | 58.90 ± 7.02 | 55.70 ± 6.88 | P > 0.05 | 12.87 ± 1.91 | 13.16 ± 2.08 | P > 0.05 |
| Cafeteria diet only (N = 6) | 54.93 ± 6.12 | 71.11 ± 5.90 | P < 0.001 | — | 7.82 ± 1.03 | P < 0.001 |
| Cafeteria diet + test formulation (N = 6) | 56.35 ± 6.31 | 64.01 ± 4.87 | P < 0.01 | — | 11.02 ± 1.94 | P < 0.01 |

TABLE 4

Role of test formulation on Total Cholesterol among high cholesterol diet treated rats

| Treated group | Total cholesterol level (mg/dl) Initial | After 15 Days | After 1 months |
|---|---|---|---|
| Normal control (N = 10)* | 64.32 ± 7.89 | 63.80 ± 6.52 | 64.70 ± 8.42 |
| High cholesterol diet (N = 10)** | — | 895.42 ± 49.75 | 480.82 ± 40.72 |
| High cholesterol diet + test formulation (N = 10)*** | — | 688.59 ± 101.22 | 402.71 ± 45.90 |
| High cholesterol diet + statin (2.5 mg/kg/day) (N = 10)**** | — | 691.52 ± 78.85 | 280.50 ± 16.80 |

Comp.
| | | | |
|---|---|---|---|
| *vs** | P > 0.05 | P < 0.001 | P < 0.001 |
| vs* | | P < 0.001 | P < 0.001 |
| *vs** | | P < 0.001 | P < 0.001 |

TABLE 5

Effect of test formulation on HDL-c level among high cholesterol diet treated rats

| Treated group | HDL-c level (mg/dl) Initial | After 15 Days | After 1 months |
|---|---|---|---|
| Normal control (N = 10)* | 22.50 ± 4.33 | 23.32 ± 2.85 | 22.37 ± 3.85 |
| High cholesterol diet (N = 10)** | — | 17.82 ± 5.32 | 13.85 ± 1.85 |
| High cholesterol diet + test formulation (N = 10)*** | — | 18.45 ± 2.91 | 20.65 ± 2.85 |
| High cholesterol diet + statin (2.5 mg/kg/day) (N = 10)**** | — | 20.32 ± 4.85 | 21.85 ± 3.85 |

Comp.
| | | | |
|---|---|---|---|
| *vs** | P > 0.05 | P < 0.05 | P < 0.001 |
| vs* | | P > 0.05 | P < 0.001 |
| *vs** | | P > 0.05 | P < 0.05 |

TABLE 6

Effect of test formulation on LDL-c level among high cholesterol diet treated rats

| Treated group | LDL-c level (mg/dl) Initial | After 15 Days | After 1 months |
|---|---|---|---|
| Normal control (N = 10)* | 23.85 ± 4.78 | 22.75 ± 5.72 | 24.22 ± 6.85 |
| High cholesterol diet (N = 10)** | — | 341.50 ± 62.32 | 314.40 ± 48.34 |
| High cholesterol diet + test formulation (N = 10)*** | — | 270.15 ± 40.23 | 139.22 ± 30.12 |
| High cholesterol diet + statin (2.5 mg/kg/day) (N = 10)**** | — | 255.80 ± 37.38 | 108.85 ± 16.85 |

Comp.

TABLE 6-continued

Effect of test formulation on LDL-c level among high cholesterol diet treated rats

| Treated group | LDL-c level (mg/dl) | | |
|---|---|---|---|
| | Initial | After 15 Days | After 1 months |
| *vs** | P > 0.05 | P < 0.001 | P < 0.001 |
| vs* | | P < 0.05 | P < 0.001 |
| *vs** | | P > 0.05 | P < 0.05 |

TABLE 7

Effect of test formulation on Triglycerides level among high cholesterol diet treated rats

| Treated group | Triglycerides level (mg/dl) | | |
|---|---|---|---|
| | Initial | After 15 Days | After 1 months |
| Normal control (N = 10)* | 26.85 ± 8.70 | 30.32 ± 7.85 | 28.40 ± 5.52 |
| High cholesterol diet (N = 10)** | — | 340.70 ± 64.80 | 298.50 ± 39.32 |
| High cholesterol diet + test formulation (N = 10)*** | — | 241.93 ± 59.75 | 188.93 ± 28.45 |
| High cholesterol diet + statin (2.5 mg/kg/day) (N = 10)**** | — | 228.50 ± 31.80 | 112.85 ± 19.30 |

Comp.
| *vs** | P > 0.05 | P < 0.001 | P < 0.001 |
| vs* | | P < 0.05 | P < 0.01 |
| *vs** | | P > 0.05 | P < 0.05 |

Clinical Study

TABLE 1

Effect of test formulation on Body Mass Index among type-II diabetes mellitus cases

| Groups | No. of cases | Body Mass Index | | Comp. Initial vs After 6 months therapy |
|---|---|---|---|---|
| | | Initial | After 6 months therapy | |
| Conventional treatment | 34 | 31.62 ± 3.01 | 30.71 ± 3.04 | P > 0.05 |
| Conventional treatment + test formulation | 45 | 29.75 ± 2.89 | 27.73 ± 2.90 | P < 0.05 |
| Test formulation treated | 43 | 31.25 ± 2.97 | 27.94 ± 2.41 | P < 0.01 |

TABLE 2

Change in Fasting Blood Glucose level following test formulation treatment in type-2 diabetes mellitus cases

| Groups | No. of cases | Fasting blood glucose (mg/dl) | | | Comp. Initial vs After 6 months therapy |
|---|---|---|---|---|---|
| | | Initial | After 3 months therapy | After 6 months therapy | |
| Conventional treatment | 34 | 172.37 ± 24.90 | 133.23 ± 23.60 | 116.44 ± 26.24 | P < 0.001 |
| Conventional treatment + test formulation | 45 | 173.90 ± 25.82 | 122.87 ± 26.90 | 110.45 ± 12.82 | P < 0.001 |
| Test formulation treated | 43 | 161.04 ± 16.42 | 130.45 ± 10.82 | 123.97 ± 8.41 | P < 0.001 |

TABLE 3

Changes in postprandial blood glucose level following test formulation treatment in type-2 diabetes mellitus cases

| Groups | No. of cases | Postprandial blood glucose (mg/dl) | | | Comp. Initial vs After 6 months therapy |
|---|---|---|---|---|---|
| | | Initial | After 3 months therapy | After 6 months therapy | |
| Conventional treatment | 34 | 280.90 ± 29.90 | 167.03 ± 32.05 | 142.94 ± 22.36 | P < 0.001 |
| Conventional treatment + test formulation | 45 | 287.90 ± 29.82 | 174.82 ± 41.02 | 148.34 ± 31.84 | P < 0.001 |
| Test formulation treated | 43 | 261.39 ± 17.84 | 219.47 ± 13.80 | 169.42 ± 10.87 | P < 0.001 |

TABLE 4

Changes in Total cholesterol following test formulation treatment among type-2 diabetes mellitus cases

| Groups | No. of cases | Total cholesterol (mg/dl) | | | Comp. Initial vs After 6 months therapy |
|---|---|---|---|---|---|
| | | Initial | After 3 months therapy | After 6 months therapy | |
| Conventional treatment | 34 | 209.59 ± 42.97 | 202.63 ± 40.30 | 202.66 ± 39.19 | P > 0.05 |
| Conventional treatment + test formulation | 45 | 223.54 ± 32.41 | 188.01 ± 28.32 | 183.68 ± 25.56 | P < 0.05 |
| Test formulation treated | 43 | 227.10 ± 19.80 | 189.45 ± 20.73 | 173.08 ± 13.97 | P < 0.01 |

TABLE 5

Role of test formulation on the HDL-c levels among type-2 diabetes mellitus cases

| Groups | No. of cases | HDL-c (mg/dl) | | | Comp. Initial vs After 6 months therapy |
|---|---|---|---|---|---|
| | | Initial | After 3 months therapy | After 6 months therapy | |
| Conventional treatment | 34 | 46.03 ± 6.60 | 46.24 ± 5.70 | 45.90 ± 6.00 | P > 0.05 |
| Conventional treatment + test formulation | 45 | 48.90 ± 3.84 | 50.91 ± 3.56 | 53.90 ± 3.22 | P < 0.02 |
| Test formulation treated | 43 | 41.99 ± 4.11 | 46.39 ± 3.75 | 49.02 ± 2.88 | P < 0.05 |

TABLE 6

Effect of test formulation on LDL-c levels among type-2 diabetes mellitus cases

| Groups | No. of cases | LDL-c (mg/dl) Initial | After 3 months therapy | After 6 months therapy | Comp. Initial vs After 6 months therapy |
|---|---|---|---|---|---|
| Conventional treatment | 34 | 131.52 ± 6.90 | 130.63 ± 5.68 | 129.60 ± 6.02 | P > 0.05 |
| Conventional treatment + test formulation | 45 | 136.04 ± 8.11 | 122.45 ± 6.93 | 109.35 ± 6.79 | P < 0.01 |
| Test formulation treated | 43 | 138.45 ± 6.90 | 116.93 ± 7.84 | 99.85 ± 6.35 | P < 0.01 |

TABLE 7

Changes in Triglyceride content following test formulation treatment in type-2 diabetes mellitus cases

| Groups | No. of cases | Triglyceride (mg/dl) Initial | After 3 months therapy | After 6 months therapy | Comp. Initial vs After 6 months therapy |
|---|---|---|---|---|---|
| Conventional treatment | 34 | 220.46 ± 45.34 | 216.20 ± 39.27 | 217.63 ± 41.46 | P > 0.05 |
| Conventional treatment + test formulation | 45 | 241.87 ± 41.90 | 165.82 ± 46.08 | 132.42 ± 20.52 | P < 0.01 |
| Test formulation treated | 43 | 262.75 ± 38.41 | 223.78 ± 29.45 | 174.90 ± 31.65 | P < 0.001 |

TABLE 8

Changes in Apolipo (B) under influence of test formulation treatment in type-2 diabetes mellitus cases

| Groups | No. of cases | Apolipo (B) (mg/dl) Initial | After 3 months therapy | After 6 months therapy | Comp. Initial vs After 6 months therapy |
|---|---|---|---|---|---|
| Conventional treatment | 34 | 122.69 ± 20.53 | 128.76 ± 22.44 | 133.83 ± 17.80 | P < 0.05 |
| Conventional treatment + test formulation | 45 | 131.90 ± 22.87 | 115.90 ± 21.35 | 84.90 ± 16.82 | P < 0.001 |
| Test formulation treated | 43 | 128.65 ± 17.94 | 113.82 ± 10.77 | 93.82 ± 8.36 | P < 0.001 |

TABLE 9

Changes in TNF-α following test formulation treatment in type-2 diabetes mellitus cases

| Groups | No. of cases | TNF-α (pg/ml) Initial | After 3 months therapy | After 6 months therapy | Comp. Initial vs After 6 months therapy |
|---|---|---|---|---|---|
| Conventional treatment | 34 | 623.60 ± 97.35 | 535.67 ± 106.64 | 480.33 ± 106.62 | P < 0.01 |
| Conventional treatment + test formulation | 45 | 735.92 ± 114.87 | 428.90 ± 94.34 | 364.75 ± 71.38 | P < 0.001 |
| Test formulation treated | 43 | 687.42 ± 85.90 | 554.82 ± 72.85 | 461.30 ± 58.97 | P < 0.001 |

TABLE 10

Effect of test formulation on pro-inflammatory bio-markers Interleukin-6 among type-2 diabetes mellitus cases

| Groups | No. of cases | Interleukin-6 (pg/ml) Initial | After 3 months therapy | After 6 months therapy | Comp. Initial vs After 6 months therapy |
|---|---|---|---|---|---|
| Conventional treatment | 34 | 1.81 ± 0.31 | 1.79 ± 0.29 | 1.71 ± 0.31 | P > 0.05 |
| Conventional treatment + test formulation | 45 | 2.05 ± 0.23 | 1.64 ± 0.31 | 1.38 ± 0.28 | P < 0.001 |
| Test formulation treated | 43 | 1.92 ± 0.41 | 1.52 ± 0.31 | 1.26 ± 0.28 | P < 0.01 |

TABLE 11

Effect of test formulation on inflammatory marker C-reactive protein among type-2 diabetes mellitus cases

| Groups | No. of cases | CRP (mg/L) Initial | After 3 months therapy | After 6 months therapy | Comp. Initial vs After 6 months therapy |
|---|---|---|---|---|---|
| Conventional treatment | 34 | 2.36 ± 0.56 | 2.26 ± 0.53 | 2.06 ± 0.51 | P > 0.05 |
| Conventional treatment + test formulation | 45 | 3.84 ± 1.02 | 2.35 ± 0.82 | 2.09 ± 0.51 | P < 0.01 |
| Test formulation treated | 43 | 3.28 ± 0.92 | 2.38 ± 0.71 | 1.93 ± 0.24 | P < 0.01 |

TABLE 12

Homocysteine lowering effect of test formulation in type-2 diabetes mellitus cases

| Treatment group | Sex | No. of cases | Homocysteine (μmol/L) Initial | After 6 months | After 12 months | Comp. Initial vs After 12 months |
|---|---|---|---|---|---|---|
| Conventional treatment | M | 58 | 41.09 ± 3.16 | 38.42 ± 2.95 | 37.95 ± 3.10 | t = 3.72, P < 0.001 |
| | F | 29 | 35.75 ± 5.01 | 31.62 ± 3.17 | 30.88 ± 3.23 | t = 4.403, P < 0.001 |
| Conventional + Test formulation | M | 95 | 43.71 ± 4.88 | 37.71 ± 5.06 | 31.22 ± 3.97 | t = 19.394, P < 0.001 |
| | F | 42 | 38.89 ± 3.82 | 30.42 ± 2.97 | 27.46 ± 2.88 | t = 15.508, P < 0.001 |
| Treated with test formulation | M | 118 | 31.54 ± 3.17 | 29.08 ± 2.92 | 26.11 ± 2.32 | t = 15.083, P < 0.001 |
| | F | 56 | 28.77 ± 2.85 | 28.90 ± 2.98 | 26.08 ± 2.11 | t = 5.689, P < 0.001 |

We claim:

1. A herbal formulation for the treatment of vascular complications associated with type-2 diabetes mellitus consisting essentially of a therapeutically effective amount of a hydromethanolic extract of *Salacia roxburghii, Garcinia indica* and *Largerstoremia parviflora*.

2. The herbal formulation as claimed in claim 1, wherein said hydro-methanolic extract is water: methanol in a ratio of 30:70.

3. The herbal formulation as claimed in claim 1, wherein parts of the plants used for preparing the extracts are *Salacia roxburghii* Root and Fruits, *Garcinia indica* Fruits and Seeds and *Largerstroemia parviflora* Leaves.

4. The herbal formulation as claimed in claim 1, wherein the plant extracts are present in the herbal formulation in the following amounts:

| | |
|---|---|
| *Salacia roxburghii* | 225-400 mg, |
| *Garcini indica* | 175-300 mg, and |
| *Largerstroemia parviflora* | 175-325 mg. |

5. The herbal formulation as claimed in claim 1, wherein the plant extracts are present in the herbal formulation in the following amounts:

| | |
|---|---|
| *Salacia roxburghii* | 275 mg, |
| *Garcinia Indica* | 225 mg, and |
| *Largerstroemia parviflora* | 225 mg. |

6. A herbal formulation for the treatment of vascular complications associated with type-2 diabetes mellitus consisting essentially of a therapeutically effective amount of a hydromethanolic extract of *Salacia roxburghii* and *Garcinia indica*.

7. The herbal formulation as claimed in claim 6, wherein said hydromethanolic extract is water: methanol in a ratio of 30:70.

8. The herbal formulation as claimed in claim 6, wherein parts of the plants used for preparing the extract are *Salacia roxburghii* Root and Fruits, and *Garcinia indica* Fruits and Seeds.

9. The herbal formulation as claimed in claim 6, wherein the plant extracts are present in the herbal formulation in the following amounts:

| | |
|---|---|
| *Salacia roxburghii* | 225-400 mg, and |
| *Garcinia indica* | 175-300 mg. |

10. The herbal formulation as claimed in claim 6, wherein the plant extract are present in the herbal formulation in the following amounts:

| | |
|---|---|
| *Salacia roxburghii* | 275 mg, and |
| *Garcinia indica* | 225 mg. |

11. A herbal formulation for the treatment of vascular complications associated with type-2 diabetes mellitus consisting essentially of a therapeutically effective amount of a hydromethanolic extract of *Salacia roxburghii, Salacia oblonga* and *Garcinia indica*.

12. The herbal formulation as claimed in claim 11, wherein said hydromethanolic extract is water: methanol in a ratio of 30:70.

13. The herbal formulation as claimed in claim 11, wherein parts of the plants used for preparing the extract are *Salacia roxburghii* Root and Fruits, *Salacia oblonga* Root and *Garcinia indica* Fruits and Seeds.

14. The herbal formulation as claimed in claim 11, wherein the plant extracts are present in the herbal formulation in the following amounts:

| | |
|---|---|
| *Salacia roxburghii* | 225-400 mg |
| *Salacia oblonga* | 200-425 mg, and |
| *Garcinia indica* | 175-300 mg. |

15. The herbal formulation as claimed in claim 11, wherein the plant extracts are present in the herbal formulation in the following amounts:

| | |
|---|---|
| *Salacia roxburghii* | 275 mg, |
| *Salacia oblonga* | 325 mg, and |
| *Garcinia indica* | 225 mg. |

16. A herbal formulation for the treatment of vascular complications associated with type-2 diabetes mellitus consisting essentially of a therapeutically effective amount of a hydromethanolic extract of *Salacia roxburghii, Salacia oblonga, Garcinia indica* and *Lagerstroemia parviflora*.

17. The herbal formulation as claimed in claim 16, wherein said hydromethanolic extract is water: methanol in a ratio of 30:70.

18. The herbal formulation as claimed in claim 16, wherein parts of the plants used for preparing the extract are *Salacia roxburghii* Root and Fruits, *Salacia oblonga* Root, *Garcinia indica*, Fruits and Seeds, and *Largerstroemia parviflora* Leaves.

19. The herbal formulation as claimed in claim 16, wherein the plant extracts are present in the herbal formulation in the following amounts:

| | |
|---|---|
| *Salacia roxburghii* | 225-400 mg, |
| *Salacia oblonga* | 200-425 mg, |
| *Garcinia indica* | 175-300 mg, and |
| *Largerstroemia parviflora* | 175-325 mg. |

20. The herbal formulation as claimed in claim 16, wherein the plant extracts are present in the herbal formulation in the following amounts:

| | |
|---|---|
| *Salacia roxburghii* | 275 mg, |
| *Salacia oblonga* | 325 mg, |
| *Garcinia indica* | 225 mg, and |
| *Largerstroemia parviflora* | 225 mg. |

* * * * *

UNITED STATES PATENT AND TRADEMARK OFFICE
CERTIFICATE OF CORRECTION

PATENT NO. : 8,337,911 B2 
APPLICATION NO. : 13/162778 
DATED : December 25, 2012 
INVENTOR(S) : Dubey et al.

Page 1 of 1

It is certified that error appears in the above-identified patent and that said Letters Patent is hereby corrected as shown below:

On the Title Page

Item (75) Inventors should read:

Samathanam Mercy Debrah, Varanasi (IN)

Signed and Sealed this
Twenty-third Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,337,911 B2 | Page 1 of 1 |
| APPLICATION NO. | : 13/162778 | |
| DATED | : December 25, 2012 | |
| INVENTOR(S) | : Dubey et al. | |

It is certified that error appears in the above-identified patent and that said Letters Patent is hereby corrected as shown below:

On the Title Page

Item (75) Inventors should read:

<u>Samathanam</u> Mercy Deborah, Varanasi (IN)

This certificate supersedes the Certificate of Correction issued December 23, 2014.

Signed and Sealed this
Twenty-fourth Day of March, 2015

Michelle K. Lee
*Director of the United States Patent and Trademark Office*